(12) United States Patent
Granlund et al.

(10) Patent No.: US 10,311,687 B2
(45) Date of Patent: Jun. 4, 2019

(54) ENHANCING CONTROLLING OF HAPTIC OUTPUT

(71) Applicant: Polar Electro Oy, Kempele (FI)

(72) Inventors: Tommy Granlund, Oulu (FI); Mikko Tuunanen, Oulu (FI)

(73) Assignee: Polar Electro Oy, Kempele (FI)

( * ) Notice: Subject to any disclaimer, the term of this patent is extended or adjusted under 35 U.S.C. 154(b) by 7 days.

(21) Appl. No.: 15/347,436

(22) Filed: Nov. 9, 2016

(65) Prior Publication Data

US 2017/0148282 A1 May 25, 2017

(30) Foreign Application Priority Data

Nov. 24, 2015 (EP) .................... 15195981

(51) Int. Cl.
| | | |
|---|---|---|
| *A61B 5/00* | (2006.01) | |
| *A61B 5/11* | (2006.01) | |
| *G06F 1/16* | (2006.01) | |
| *G06F 3/01* | (2006.01) | |
| *G08B 6/00* | (2006.01) | |
| *A61B 5/024* | (2006.01) | |
| *A61B 5/0205* | (2006.01) | |

(52) U.S. Cl.
CPC .............. *G08B 6/00* (2013.01); *A61B 5/0205* (2013.01); *A61B 5/681* (2013.01); *A61B 5/7405* (2013.01); *A61B 5/7455* (2013.01); *G06F 1/163* (2013.01); *G06F 3/016* (2013.01); *G06F 3/017* (2013.01); *A61B 5/0022* (2013.01); *A61B 5/02416* (2013.01); *A61B 5/1112* (2013.01); *A61B 2562/0219* (2013.01); *A61B 2562/0271* (2013.01)

(58) Field of Classification Search
None
See application file for complete search history.

(56) References Cited

U.S. PATENT DOCUMENTS

| | | |
|---|---|---|
| 8,493,354 B1 | 7/2013 | Birnbaum et al. |
| 2003/0181116 A1 | 9/2003 | Van Heerden et al. |
| 2009/0167677 A1 | 7/2009 | Kruse et al. |
| 2011/0098029 A1 | 4/2011 | Rhoads et al. |
| 2012/0274508 A1 | 11/2012 | Brown et al. |
| 2012/0326873 A1 | 12/2012 | Utter, II |
| 2014/0031703 A1 | 1/2014 | Rayner et al. |
| 2014/0055358 A1 | 2/2014 | Birnbaum et al. |

(Continued)

OTHER PUBLICATIONS

Partial European Search Report, Application No. EP 15 19 5981, 5 pages, dated May 4, 2016.

(Continued)

*Primary Examiner* — Nay Tun
*Assistant Examiner* — Shawna M Kingston
(74) *Attorney, Agent, or Firm* — FisherBroyles, LLP

(57) ABSTRACT

A method in an activity tracking apparatus configured to be worn by a user includes obtaining, by the activity tracking apparatus, motion data from one or more sensors, wherein the motion data characterizes motion of the activity tracking apparatus; and controlling, based on the motion data, characteristics of a vibration causing a haptic output, wherein the haptic output is configured to be output as a response to an event on the activity tracking apparatus. Corresponding apparatus and computer programs are also disclosed.

19 Claims, 9 Drawing Sheets

(56) References Cited

U.S. PATENT DOCUMENTS

| | | |
|---|---|---|
| 2014/0104165 A1 | 4/2014 | Birnbaum et al. |
| 2014/0197946 A1 | 7/2014 | Park et al. |
| 2014/0232534 A1 | 8/2014 | Birnbaum et al. |
| 2014/0278139 A1 | 9/2014 | Hong et al. |
| 2014/0278220 A1 | 9/2014 | Yuen |
| 2015/0160728 A1* | 6/2015 | Yagi .................. H04M 1/72569 345/156 |

OTHER PUBLICATIONS

European Search Report, Application No. EP 15 19 5981, 7 pages dated Sep. 23, 2016.

* cited by examiner

ENHANCING CONTROLLING OF HAPTIC OUTPUT

CROSS-REFERENCE TO RELATED APPLICATION

This application claims benefit to European Application No. 15195981.4, filed Nov. 24, 2015, which is incorporated by reference herein in its entirety.

BACKGROUND

Field

This invention relates to controlling haptic output of a training device.

Description of the Related Art

Training devices are used in many different situations. Haptic output may be used to indicate an event to a user of the training device. Therefore, enhancing control of the haptic output may be beneficial to enhance the user experience provided by the training device.

SUMMARY

According to an aspect, there is provided a method in an activity tracking apparatus configured to be worn by a user, the method comprising: obtaining, by the activity tracking apparatus, motion data from one or more sensors, the motion data characterizing motion of the activity tracking apparatus; and controlling, based on the motion data, characteristics of a vibration causing a haptic output, wherein the haptic output is configured to be output as a response to an event on the activity tracking apparatus, wherein the activity tracking apparatus comprises a plurality of modes, the characteristics of the vibration being configurable in each of the plurality of modes respectively.

According to an aspect, there is provided an apparatus comprising: at least one processor, and at least one memory comprising a computer program code, wherein the at least one memory and the computer program code are configured, with the at least one processor, to cause an activity tracking apparatus to perform operations comprising: obtaining motion data from one or more sensors, the motion data characterizing motion of the activity tracking apparatus; and controlling, based on the motion data, characteristics of a vibration causing a haptic output, wherein the haptic output is configured to be output as a response to an event on the activity tracking apparatus, wherein the activity tracking apparatus comprises a plurality of modes, the characteristics of the vibration being configurable in each of the plurality of modes respectively.

According to an aspect, there is provided a non-transitory computer readable storage medium comprising program instructions which, when loaded into an activity tracking apparatus cause the activity tracking apparatus to perform operations comprising: obtaining motion data from one or more sensors, the motion data characterizing motion of the activity tracking apparatus; and controlling, based on the motion data, characteristics of a vibration causing a haptic output, wherein the haptic output is configured to be output as a response to an event on the activity tracking apparatus, wherein the activity tracking apparatus comprises a plurality of modes, the characteristics of the vibration being configurable in each of the plurality of modes respectively.

Some embodiments are defined in the dependent claims.

One or more examples of implementations are set forth in more detail in the accompanying drawings and the description below. Other features will be apparent from the description and drawings, and from the claims.

BRIEF DESCRIPTION OF DRAWINGS

In the following the invention will be described in greater detail by means of preferred embodiments with reference to the attached drawings, in which.

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
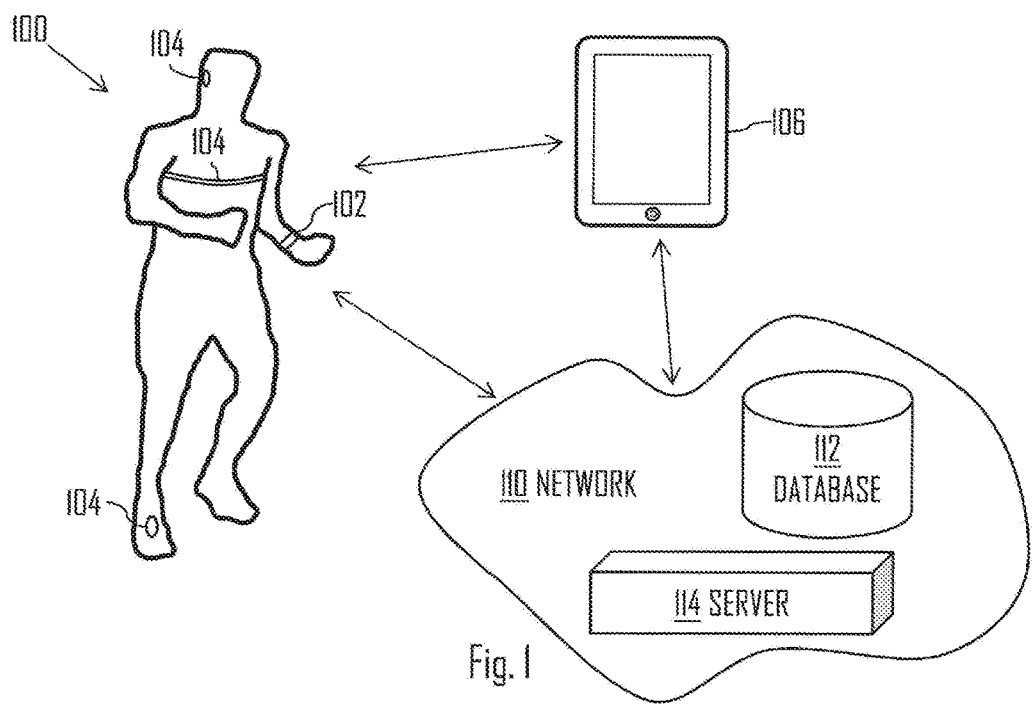
FIG. 1 illustrates an example system to which the embodiments of the invention may be applied.

FIG. 1 illustrates a system to which embodiments of the invention may be applied. Said system may be used to monitor physical training, activity, and/or inactivity of a user 100. Thus, the embodiments may not be limited to monitoring and/or measuring physical training of the user 100, and thus said system may be used to monitor physical activity and/or inactivity during the day and/or night (e.g. 24 hours a day). Such may be possible using one or more devices described in relation to FIG. 1 and in the embodiments below.

Referring to FIG. 1, the user 100 may wear a wearable device, such as a wrist device 102. In another example, the wearable device may be and/or be comprised in glasses. Due to simplicity reasons, let us now describe the wearable device as being the wrist device 102. However, at least some embodiments described in relation to wrist device 102 may be utilized by other wearable devices. The wrist device 102 may be, for example, a smart watch, a smart device, sports watch, and/or an activity tracking apparatus (e.g. bracelet, arm band, wrist band, mobile phone, glasses). In an embodiment, the wrist device 102 is an activity tracking apparatus. This may mean that said apparatus may be worn in other parts of the user 100, such as but not limited to forearm, bicep area, neck, forehead, and/or leg.

The wrist device 102 may be used to monitor physical activity of the user 100 by using data from internal sensor(s) comprised in the wrist device 102, data from external sensor device(s) 104, and/or data from external services. It may be possible to receive physical activity-related information from a network 110, as the network may comprise, for example, physical activity-related information of the user 100 and/or some other user(s). Thus, the wrist device 102 may be used to monitor physical activity-related information of the user 100 and/or the other user(s). Naturally, one or more of the external sensor device(s) 104 may be worn by the other user(s), and thus information received from said one or more sensor device(s) 104 may be monitored from the wrist device 102 by the user 100.

It needs to be understood that the wrist device 102 may be used to monitor physical activity of the user 100 and/or to be used as a smart watch configured to enable communication with, for example, a portable electronic device 106, the network 110, and/or some other network, such as a cellular network. Thus, for example, the wrist device 102 may be connected (i.e. wirelessly connected) to the portable electronic device 106, such as a mobile phone, smart phone, tablet and/or computer to name a few. This may enable data transfer between the wrist device 102 and the portable electronic device 106. The data transfer may be based on Bluetooth protocol, for example. Other wireless communication methods, such as Wireless Local Area Network (WLAN) and/or Near Field Communication (NFC), may also be used.

In case of communicating directly with the cellular network, the wrist device 102 may comprise similar communication capabilities as mobile devices, such as 2G, 3G, LTE, LTE-A, 4G and/or 5G communication capabilities. Thus, for example, the wrist device 102 may comprise the communication circuitry capable of operating on said technologies, a Subscriber Identification Module (SIM) and/or a memory comprising a virtual SIM configured to provide a secured identification for the wrist device 102 when operating with the cellular network.

The wrist device 102 may be used to monitor activity and/or inactivity of the user 100. Similarly, the portable electronic device 106 may be used to monitor the activity and/or inactivity of the user 100. Such may require the portable electronic device 106 to acquire physical activity-related data from the wrist device 102, some other wearable device, and/or from external sensor device(s) 104. However, it may be that the portable electronic device 106 determines activity and/or inactivity of the user 100 by utilizing internal sensor(s), such as accelerometer or satellite positioning circuitry.

The wrist device 102 may comprise a cardiac activity circuitry (e.g. cardiac activity circuitry 374 shown in FIG. 3B) configured to determine cardiac activity of the user 100, such as heart rate, Heart Beat Interval (HBI) and/or Heart Rate Variability (HRV), for example. The cardiac activity circuitry may comprise an optical cardiac activity sensor, such as a PPG (photoplethysmography) sensor, configured to measure cardiac activity of the user 100. The optical cardiac activity sensor may detect the cardiac activity of the user 100 by optical measurement, which may comprise sending a light beam towards skin of the user 100 and measuring the bounced and/or emitted light from the skin of the user 100. The light beam may alter when travelling through veins of the user 100 and the alterations may be detected by the optical cardiac activity sensor. By using the detected data, the wrist device 102, may determine cardiac activity of the user 100, such as heart rate for example.

Figure 3A:
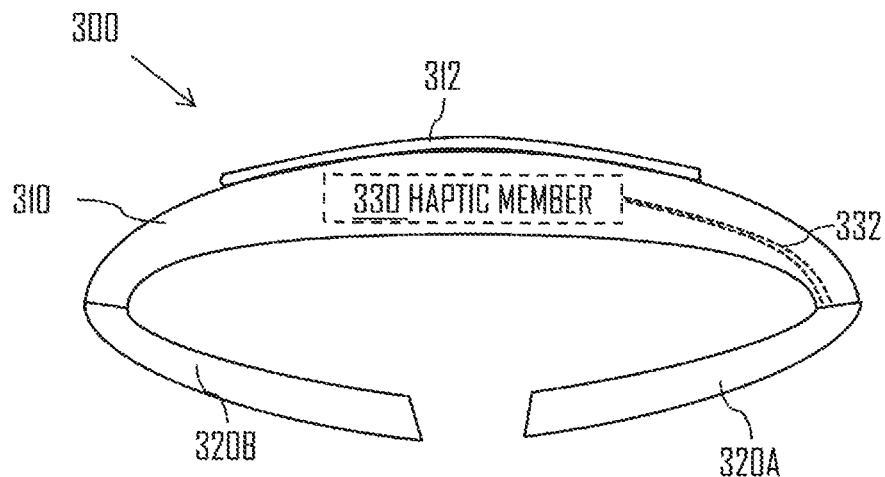
FIGS. 3A to 3B illustrate some embodiments.
Figure 3B:
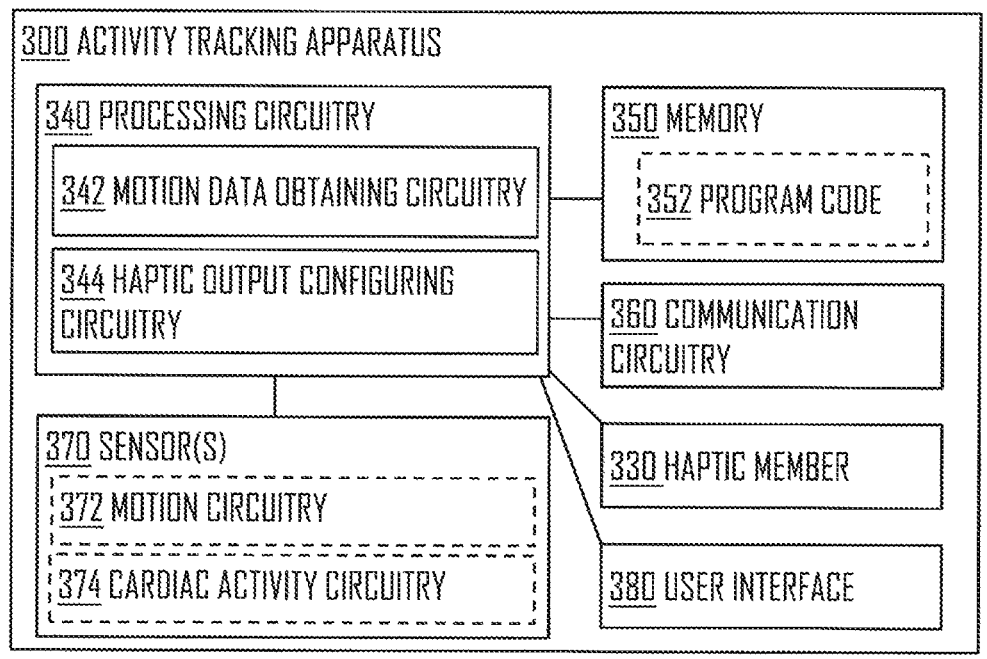

The activity tracking apparatus 300 shown, for example, in FIG. 3B (e.g. the wrist device 102) may comprise a bioimpedance sensor. The bioimpedance sensor may be configured measure cardiac activity of the user 100, for example. The bioimpedance sensor may be or comprise a skin conductance sensor configured to measure skin conductance, for example. The bioimpedance measurement may be based on transmitting a radio signal into the skin of the user 100, and observing changes in the radio signal due to impedance changes caused by, for example, blood volume changes. Thus, for example, cardiac activity of the user 100 may be determined by the wrist device 102 from the data produced by the bioimpedance sensor. Bioimpedance sensors(s) of the activity tracking apparatus 300 may be used for one or more types of measurements. For example, the bioimpedance sensor may be used to measure skin conductance and/or cardiac activity of the user 100.

In an embodiment, the cardiac activity circuitry comprises the bioimpedance sensor described above.

In an embodiment, the bioimpedance sensor is a separate entity. That is, it may be used separately and/or independently compared with the cardiac activity sensor. Thus, for example, the wrist device 102 may comprise a cardiac activity circuitry and a bioimpedance sensor(s). Further, the cardiac activity circuitry may comprise a further bioimpedance sensor(s).

Further, also other types of biosignal measurement sensors may be embedded into the activity tracking apparatus 300 (e.g. the wrist device 102). These types include but are not limited to the following: a Laser Doppler-based blood flow sensor, a magnetic blood flow sensor, an Electromechanical Film (EMFi) pulse sensor, a polarization blood flow sensor, an Electrocardiography (EKG) sensor comprising at least one electrode. Such sensors may be used, for example, to determine cardiac activity of the user 100.

It also needs to be noted that the cardiac activity circuitry may produce raw measurement data of the cardiac activity and/or it may process the measurement data into cardiac activity information, such as heart rate for example. The sensor(s) in the cardiac activity circuitry may comprise data processing capabilities. Also, the wrist device 102 and/or some other wearable device may comprise a processing circuitry configured to obtain the cardiac activity measurement data from the cardiac activity circuitry and to process said data into cardiac activity information, such as a cardiac activity metric characterizing the cardiac activity of the user 100. For example, the measurement data of the optical cardiac activity sensor may be used, by the processing circuitry, to determine heart rate, HRV and/or HBI of the user 100. Further, the raw measurement data and/or processed information may be processed by the wrist device 102 or some other wearable device, and/or transmitted to an external device, such as the portable electronic device 106.

In an embodiment, the wrist device 102 comprises a motion circuitry (e.g. motion circuitry 372 shown in FIG. 3B) configured to measure motion induced by the user 100 to the wrist device 102 by moving hand (or other body parts to which the wrist device is attached to) in which the user 100 wears the wrist device 102. As described above, the motion circuitry may also be comprised in some other wearable device and/or in the portable electronic device 106. Further, at least one of the external sensor device(s) 104 may comprise the motion circuitry. Thus, the motion of the user 100 may be determined in one or more devices of the activity tracking system.

The motion circuitry may use other motion data, such as location data of the user, to determine motion of the user 100. For example, the motion circuitry may comprise a satellite positioning circuitry, such as a global navigation satellite system (GNSS) circuitry. The GNSS circuitry may comprise, for example, a Global Positioning System (GPS) and/or a GLObal NAvigation Satellite System (GLONASS). The satellite positioning circuitry may be used for receiving satellite positioning data. The satellite positioning data may be used, by the wrist device 102, to determine motion and/or location of the user 100.

In an embodiment, the motion circuitry comprises at least one of the following: an accelerometer, a magnetometer, and a gyroscope.

In an embodiment, the motion circuitry comprises an accelerometer and a gyroscope. The motion circuitry may further comprise sensor fusion software for combining the accelerometer data and gyroscope data so as to provide physical quantities, such as acceleration data, velocity data, or limb trajectory data in a reference coordinate system having orientation defined by a predetermined gyroscope orientation.

In an embodiment, the motion circuitry comprises a gyroscope and a magnetometer. The motion circuitry may further comprise sensor fusion software to combine gyroscope data and magnetometer data so as to provide a reference coordinate system for the gyroscope based on the Earth magnetic field measured by the magnetometer. In general, the sensor fusion software described above may combine measurement data acquired from at least two motion sensors such that measurement data acquired from one motion sensor is used to establish the reference coordinate system for the measurement data acquired from at least one other motion sensor. Thus for example, the satellite positioning data may also be utilized in the sensor fusion.

It needs to be noted that even though some embodiments are described using the wrist device 102 as an example, at least some of the embodiments may be used with some other activity tracking apparatus. For example, the motion circuitry and/or some other sensors, described as a part of the wrist device 102, may be comprised in the activity tracking apparatus 300 of FIG. 3B, i.e. some other type of activity tracking apparatus than the wrist device 102 (e.g. the portable electronic device 106). The activity tracking apparatus 300 of FIG. 3B may comprise the wrist device 102 or some other device for determining activity of the user 100.

Still referring to FIG. 1, the system may further comprise the external sensor device(s) 104 used by the user 100. The external sensor device(s) 104 may comprise sensor(s) worn by the user 100 and/or sensor which may be used by the user 100. For example, a heart rate belt may be worn by the user 100. Another example may be a weight sensor (e.g. a scale) which may be occasionally used by the user 100. Other examples may comprise bike sensor(s), motion sensor(s), and temperature sensor(s), to name a few examples.

The external sensor device(s) 104 may comprise sensors, such as a heart rate transmitter, heart rate sensor, a stride sensor, a positioning sensor, a bioimpedance sensor, a cadence sensor, and a power sensor, to mention a few. The heart rate transmitter may comprise at least one electrical, optical and/or bioimpedance sensor to measure heart activity of the user 100. The electrical sensor(s) may be, for example, based on EKG measurement. The positioning sensor may comprise a satellite positioning circuitry (e.g. GPS, GLONASS), a magnetometer and/or a Bluetooth sensor. Thus, the positioning may be based on, for example, GPS location and/or Bluetooth location. The magnetometer may provide direction data based on magnetic fields on earth and/or inside structures. The bioimpedance sensor may be used to determine skin conductance of the user 100, for example.

The external sensor device(s) 104 may comprise a head sensor. The head sensor may be configured to measure cardiac activity and/or skin conductance of the user 100, for example. The head sensor may be, for example, an ear sensor which may be placed in physical connection with an ear and/or ears of the user 100. The placement may be similar to placing earplug headphones, for example. Another example may be to use a clip mechanism and/or glue-like material for the physical connection. The head sensor may utilize electrodes, optical measurement and/or bioimpedance measurement for the cardiac activity measurement, for example.

In an embodiment, the ear sensor is an in-ear sensor.

In an embodiment, the external sensor device(s) 104 comprise the ear sensor, such as the in-ear sensor. As described, the ear sensor may be used to measure, for example, cardiac activity of the user 100.

In an embodiment, the head sensor is comprised in glasses. In such case the head sensor may be comprised in earpiece(s) of the glasses, for example.

In an embodiment, the head sensor is comprised in headphones and/or earphones.

In an embodiment, the external sensor device(s) 104 comprise at least one of a cadence sensor, a speed sensor, a power sensor used in a bicycle.

In an embodiment, the external sensor device(s) 104 comprise a cadence sensor configured to be used to determine cadence during swimming. For example, such cadence sensor may be attached to wrist of the user 100 to determine strokes during swimming.

The external sensor device(s) 104 may transmit the sensor data to the wrist device 102, to some other wearable device, to the portable electronic device 106 and/or to a server 114, wherein the server is accessible via a network 110. The wrist device 102, the portable electronic device 106 and/or the server 114 may receive the sensor data.

The external sensor device(s) 104, the wrist device 102, the portable electronic device 106 and/or the server 114 may each further comprise a communication circuitry, such as wireless communication circuitry, configured to enable sensor data transfer between the external sensor device(s) 104, wrist device 102, portable electronic device 106 and/or the server 114.

Further, the wrist device 102 and/or the portable electronic device 106 may comprise a memory, wherein the memory may be used by the devices to store the data from different sensor device(s). The server 114 may use a database 112, such as a training database, to store the said data. The database 112 may be accessible via the network 110.

In an embodiment, at least some of the external sensor device(s) 104 are comprised in the wrist device 102.

In an embodiment, the wrist device 102 comprises at least one of the following sensors: a temperature sensor, a pressure sensor.

Activity tracking apparatuses (e.g. wrist device 102, wearable devices, portable electronic device 106, external sensor device(s) 104, server 114), as described above, may be used in various ways to measure and/or monitor physical activity of the user 100. On the other hand, the activity tracking apparatuses may comprise functionalities going beyond the activity tracking function. For example, the wrist device 102 may be used during training, normal every-day activities, and sleep. Further, the wrist device 102 may be used to indicate phone calls and social media messages, for example. This may mean that the activity tracking apparatus in question may be multifunctional meaning that it may need to be adaptable to different situations.

The activity tracking apparatus may indicate an event (e.g. phone call, exceeding of a heart rate zone), wherein the indication comprises a haptic output. The haptic output may be outputted together with sound and/or visual output. On the other hand, the haptic output may be enough in some cases without the sound or visual output. However, in some cases the haptic output may be too strong (e.g. when the user 100 is in a meeting), or too small (e.g. user is performing intense exercise). Therefore, there is provided a solution to enhance control of the haptic output. The solution may enhance the control of the haptic output such that the haptic output may be configurable according to the different use cases.

Figure 2:
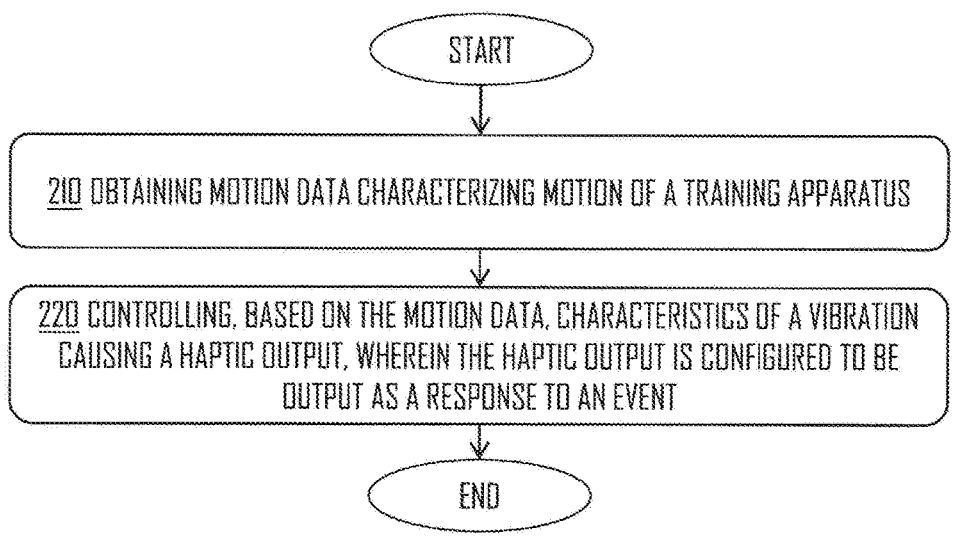
FIG. 2 illustrates a flow diagram according to an embodiment of the invention.

FIG. 2 illustrates a flow diagram according to an embodiment of the invention. Referring to FIG. 2, an activity tracking apparatus (ATA) may obtain motion data from one or more sensors, the motion data characterizing motion of the activity tracking apparatus (block 210). In step 220, the ATA may control, based on the motion data, characteristics of a vibration causing a haptic output, wherein the haptic output is configured to be output as a response to an event on the activity tracking apparatus. The ATA may be configured to be worn by the user 100.

In an embodiment, the ATA controls the characteristics of the vibration based on acceleration data of the motion data. For example, if the ATA determines higher accelerations, it may control the vibration to have a higher amplitude or higher frequency.

The ATA may be and/or comprise the wrist device 102, the portable electronic device 106, the external sensor device(s), and/or some other wearable device. For example, the portable electronic device 106 may be worn by the user 100 on an arm holster or in pocket of a garment, bag, or case. Similarly, for example, a head sensor or hear rate belt may be worn by the user 100 such that the haptic output is detectable by the user 100. The ATA may be referred to as a physical activity tracking apparatus, a training apparatus, or a physical exercise monitor, for example.

Let us now look closer on the ATA with reference to some embodiments shown in FIGS. 3A to 3B. Referring to FIG. 3A, the ATA 300 may be the ATA described in relation to FIG. 2. The ATA 300 of FIG. 3A may comprise a body 310. The ATA 300 may comprise an attachment element 320A, 320B. The attachment element 320A, 320B may comprise a strap and/or some locking mechanism enabling the ATA 300 to be detachably attached to the user 100. For example, the attachment element 320A, 320B may comprise the strap of the wrist device 102.

The ATA 300 may comprise a display 312. The display may be used to display information and/or to operate as a touch-screen interface of the ATA 300.

The ATA 300 may comprise a haptic member 330. The haptic member 330 may comprise one or more Linear Resonant Actuators (LRAs) and/or one or more vibration motors. The vibration motors may comprise an eccentric element which may cause the vibration, and consequently haptic output, as the eccentric element rotates.

In an embodiment, the vibration causing the haptic output is produced by a haptic member 330 of the ATA 300. In another example, the ATA 300 may control a haptic member of an external device (e.g. external sensor device(s) 104, wrist device 102). Thus, it may be possible that, for example, a portable electronic device 106, when used as an ATA, controls vibration by a haptic member comprised in the wrist device 102. It may also be possible that more than one haptic member is controlled. This may mean that the ATA 300 may control the haptic member 330 and/or some other haptic members which may be comprised in the ATA 300, in some other ATA, or in an external sensor, for example.

The haptic member 330 may produce vibration causing the haptic output. The vibration needs to be understood in a broad sense. The vibration may be back and forth motion to at least one direction. The vibration may comprise movement to one or more directions. The vibration may be reversible spatial motion in at least one degree of freedom. In an embodiment, the vibration comprises two-dimensional movement. In an embodiment, the vibration comprises three-dimensional movement.

Still referring to FIG. 3A, the vibration is produced by the haptic member 330 such that the haptic output is transferred via the body 310, the display 312, the attachment element 320A, 320B (e.g. a fastening strap), and/or some other element of the ATA 300. For example, the vibration caused by the haptic member 330 may propagate via the body 310 to a skin of the user 100 when the ATA 300 is worn by the user in his/her wrist.

In an embodiment, the body 310 comprises a back cover. The vibration may be beneficial to be conveyed to the back cover which may be configured to be placed against a skin of the user 100. This may be the case, for example, with wrist device 102, wherein the back cover of the wrist device 102 may be against the skin of the user 100. Thus, the haptic output may be better detected.

In an embodiment, the ATA 300 comprises a member 332 for transferring the vibration to the attachment element 320A, 320B, to the display 312, to the body 310, and/or to the back cover. The member 332 may be operatively connected to the haptic member 330, thus enabling the vibration (i.e. vibration energy) to transfer at least partly from the haptic member 330 to some other element of the ATA 300. For example, for the wrist device 102 it may beneficial that the haptic member 330 is arranged such that the vibration causes haptic output via the wrist strap of the wrist device 102. For example, one part of the member 332 may connected to the haptic member 330 and another part may be connected to some other element of the ATA 300. This may allow the vibration energy to transfer from the haptic member 330 to said some other element (e.g. display 312).

In an embodiment, the wrist strap comprises silicon and/or is made of silicon.

It may also be possible that the haptic member 330 is directly connected to the body 310, the display 312, to the attachment element 320A, 320B, and/or to some other element of the ATA 300. Thus, there may not be a need to use the member 332 to transfer the vibration. In one example, the haptic member 330 is physically connected to the body 310, thus enabling the vibration to be transferred via the body 310 to the attachment element 320A, 320B and/or to the display 312, and further to cause the haptic output detectable by the user 100. Similarly, the haptic member 330 may be operatively connected to the attachment element 320A, 320B (e.g. wrist strap) of the ATA 300.

Referring to FIG. 3B, the ATA 300 may comprise a processing circuitry 340, such as at least one processor, and at least one memory 350 including a computer program code (software) 352, wherein the at least one memory and the computer program code are configured, with the at least one processor, to cause the ATA 300 to carry out any one of the embodiments of FIGS. 2 to 8B, or operations thereof. These may comprise, for example, steps of FIG. 2.

In an embodiment the ATA 300 is comprised in the wrist device 102, the portable electronic device 106, and/or some other wearable device.

In an embodiment, the processing circuitry 340 comprises a motion data obtaining circuitry 342 configured to obtain motion data from one or more sensors, the motion data characterizing motion of the ATA 300. The processing circuitry 340 may further comprise a haptic output configuring circuitry 344 configured to control, based on the motion data, characteristics of a vibration causing a haptic output, wherein the haptic output is configured to be output as a response to an event on the ATA 300.

The ATA 300 may comprise the haptic member 330 as described above. The ATA 300 may comprise communication circuitry 360 configured to enable the ATA 300 to communicate with external devices. The communication may be wired and/or wireless. For example, the communication circuitry 360 may enable communication according to Bluetooth, Bluetooth Light Energy or Bluetooth Smart (BLE), NFC, WLAN, and/or LAN technologies. The ATA 300 may comprise one or more ports for wired connection (e.g. USB port). The ATA 300 may comprise one or more antennas to enable the communication circuitry 360 to transfer electromagnetic energy via air-interface. The communication circuitry may be a radio communication circuitry.

In an embodiment, the one or more sensors, used to acquire the motion data, are comprised in the ATA 300, and wherein the one or more sensors comprise at least one of an acceleration sensor, gyroscope, magnetometer, satellite positioning circuitry, radio communication circuitry. Looking at the example of FIG. 3B, the ATA 300 may comprise the sensors 370, wherein the sensor(s) 370 may comprise motion circuitry 372 and/or cardiac activity circuitry 374. Further, as explained, the ATA 300 may comprise the radio communication circuitry 360. The motion circuitry 372 and the cardiac activity circuitry 374 were discussed broadly in relation to FIG. 1. The motion circuitry 372 may be used to determine the motion of the ATA 300 and/or the user 100. Further, the ATA 300 may comprise some other sensors, such as a bioimpedance sensor. These were discussed broadly with reference to FIG. 1 using the wrist device 102 as an example ATA.

Further, the ATA 300 may comprise a user interface 380 comprising, for example, the display 312 and/or some other display(s), at least one keyboard, at least one button, and/or at least one speaker. The user interface 380 may enable the user 100 to input information to the ATA 300. For example, the user characteristics may be inputted which may be used to determine, by the ATA 300, maximum heart rate value for the user 100. The haptic member 330 may be understood as a separate part of the user interface 380. However, in an embodiment, the haptic member 330 may be a part of the user interface 380.

Let us now consider what kind of events there may be on the ATA 300. One example of such may be the target cadence indication explained later in more detail. Other examples may include maximum heart rate indication, or exceeding of a certain heart rate zone. In one example, the vibration may be produced by the ATA 300 such that there is a certain period between two consecutive vibration sequences. The duration of said period may indicate certain things. For example, the period may indicate how close the heart rate of the user 100 is from maximum heart rate, or from target heart rate. Another example may be to indicate, using said period, how close current speed of the user 100 is from a target speed. For example, if said period becomes close to zero (i.e. there is no space between said vibration sequences or there is only one sequence instead of two), it may be an indication that the user 100 is on the right speed or heart rate zone. On the other hand, if the two sequences are far from each other (i.e. the period is longer), it may indicate that the speed or heart rate is not in the target zone. The event examples described here need to be understood as examples, and thus there may be more different types of events. These may comprise phone calls, inactivity alerts, social media notifications, to name a few examples.

Figure 4A:
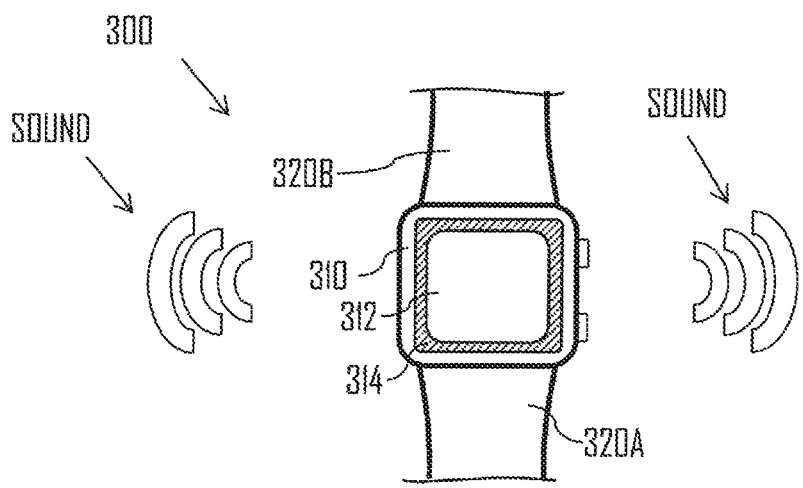
FIGS. 4A to 4B illustrate some embodiments.
Figure 4B:
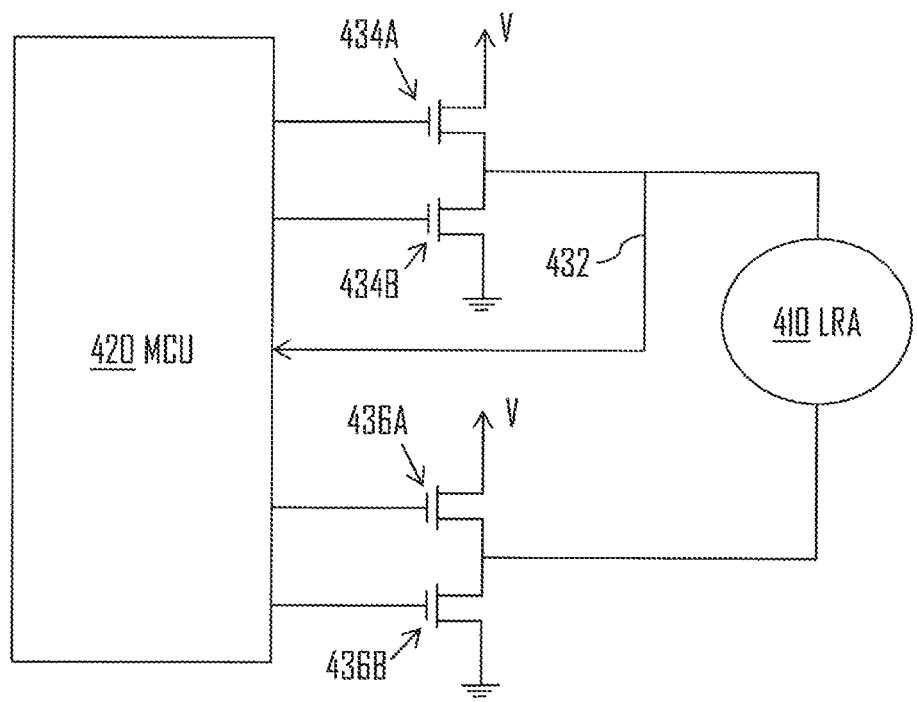

FIGS. 4A to 4B illustrate some embodiments. Referring to FIG. 4A, the ATA 300 may be illustrated such that display 312 is shown from the direction it is configured to be viewed. In FIG. 4A, the ATA 300 is illustrated as a wrist device (e.g. wrist device 102), but as said, the ATA 300 may also be some other device.

In an embodiment, the haptic member 330 is configured such that the vibration, produced by the haptic member 330, causes at least one element of the ATA 300 to produce audible sound according to the vibration. The audible sound may refer to vibration frequencies which the user 100 is able to hear. This may be beneficial as in such case there may no reason to use a further speaker as the haptic member 330 may act as an audio and vibration source.

The audible sound may be produced by the vibration by the haptic member 330. This may mean that the haptic member 330 vibrates such that the audio is produced. Another example is that the vibration by the haptic member 330 causes the body 310 and/or the display 312 to vibrate and to produce audio. The vibration frequency of the haptic member 330 may be different to that of the actual produced audio as the frequency may change when it transfers between elements.

In an embodiment, the display 312 comprises a cover 314 which is arranged and dimensioned to conceal at least a part of the display 312. The member 332 may be connected to the display 312 from the concealed area. Thus, the member 332 may be not visible to the user 100, but it may be used to transfer the vibration to the display 312 from the haptic member 330. Thus, the display 312 may produce sound towards the viewer (e.g. user 100). The member 332 may comprise a rod or similar. The member 332 may be referred to as, for example, a vibration transfer member.

It needs to be understood that at the same time as the audible sound is produced, there may also be a haptic output. Thus, the two may be outputted together or separately. Therefore, there is also provided a haptic member (e.g. haptic member 330) configured to cause producing of sound. For example, the audible sound may vary, for example, between 31 Hz and 1 kHz. Naturally, for different individuals the hearing range may be different.

One example of an audio producing structure may be shown in FIG. 4B. Referring to FIG. 4B, a LRA 410 may be or be comprised in the haptic member 330. Also a vibration motor may be used instead or together with the LRA 410. However, due to simplicity the transistor bridge (H-bridge) of FIG. 4B is illustrated only with the LRA 410.

A microcontroller (MCU) 420 may be comprised in the ATA 300. For example, the MCU 420 may be or be comprised in the processing circuitry 340. Similarly, the transistors 434A, 434B, 436A, 436B may be comprised in the ATA 300.

The shown structure of FIG. 4B may enable the LRA 410 to be inputted with a signal that causes the LRA 410 to produce vibration that causes haptic output and/or audible sound. It may be beneficial to use LRA 410 as the vibration source for producing audible sound as power consumption of the LRA 410 may be rather small.

In an embodiment, the input signal and/or the LRA 410 is configured to vibrate on at least one natural frequency. This may reduce the amount of harmonic distortion(s).

In an embodiment, the LRA 410 and/or the haptic member 330 is separated from at least one element of the ATA 300 with elastic material, such as rubber or silicon. One example of such element may be the back cover of the ATA 300. It is possible to separate the LRA 410 and/or the haptic member 330 from some other elements of the ATA 300 with elastic material. This may enable, for example, the sound producing by causing the display to resonate, but at least dampen the haptic output to the user 100. This may be beneficial in order to attain both good audio output and good haptic output.

In an embodiment, the structure of FIG. 4B comprises a coupling 432 enabling the LRA 410 to produce a signal according to a user input (e.g. tap on the ATA 300 by the user 100), wherein said signal may be detected by the MCU 420. Thus, the shown structure of FIG. 4B may enable the ATA 300 to determine the user input, such as said tap, and cause a function on the ATA according to the user input. As said, the structure of FIG. 4B may be comprised in the ATA 300, for example.

Let us now look closer on how the vibration causing the haptic output may be controlled. As described above, the vibration needs to be understood in a broad sense. More particularly, it is possible that the haptic output, described in relation to FIG. 2, may be produced by forces, vibrations, or motions applied to the user 100 by the haptic member 330. The haptic output may be detectable as it may recreate a sense of touch to the user 100.

Figure 5A:
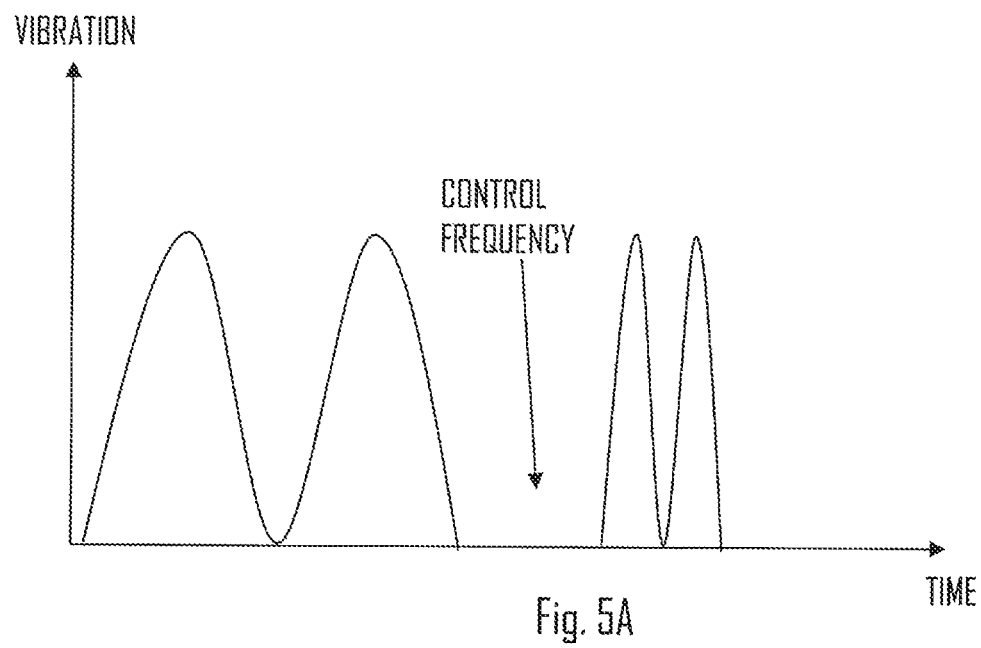
FIGS. 5A to 5F illustrate some embodiments.
Figure 5B:
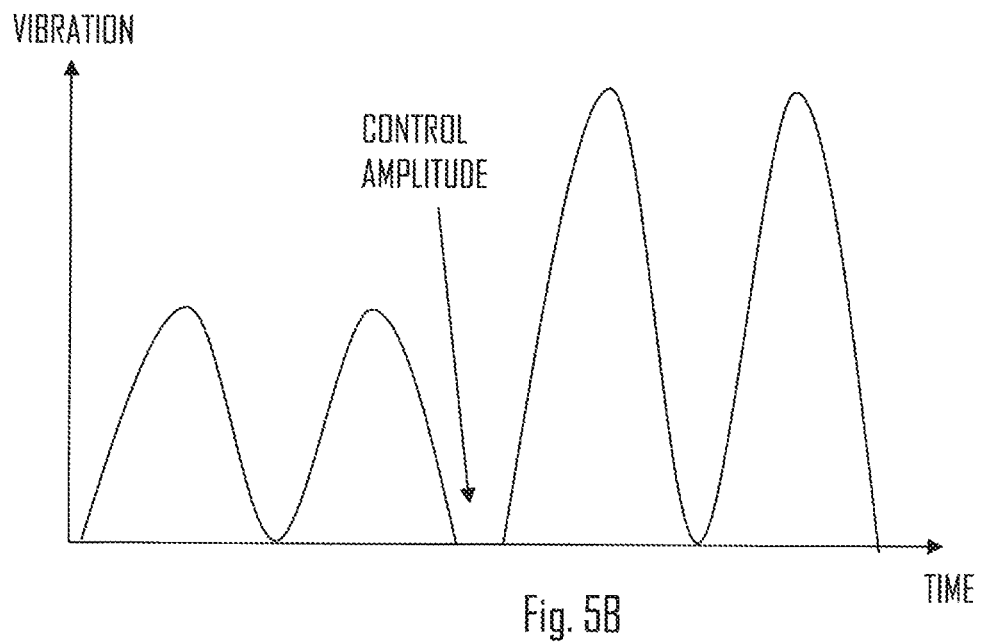
Figure 5C:
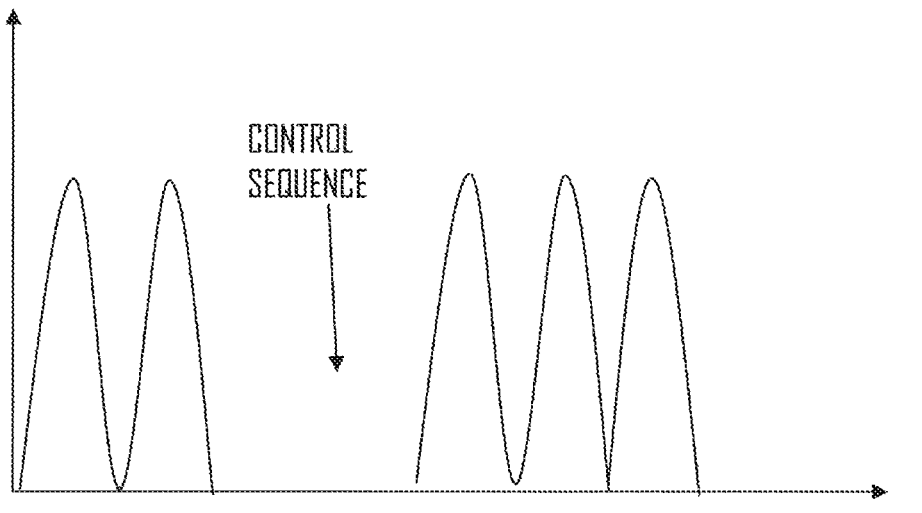
Figure 5D:
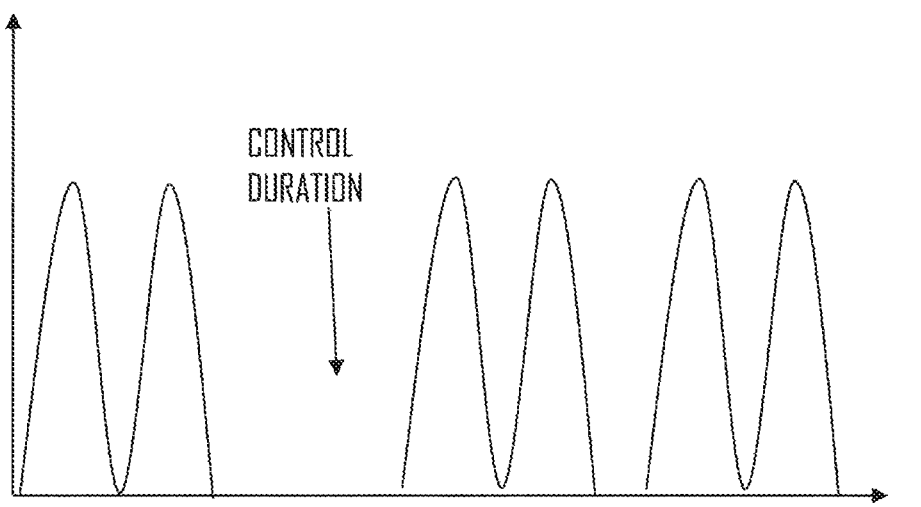
Figure 5E:
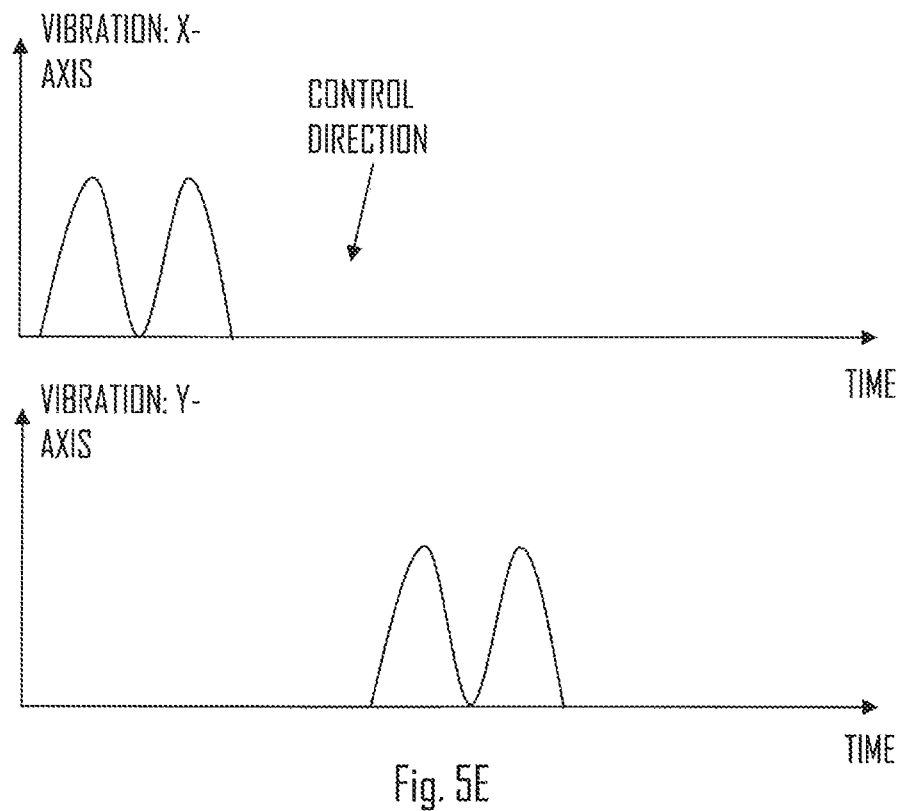

Referring to FIGS. 5A to 5E, the controlling the characteristics of the vibration causing the haptic output comprises controlling frequency of the vibration (example in FIG. 5A), amplitude of the vibration (example in FIG. 5B), sequence of the vibration (example in FIG. 5C), duration of the vibration (example in FIG. 5D), and/or dimension of the vibration (example in FIG. 5E). Let us go through each of these examples.

Referring to FIG. 5A, the ATA 300 may control the frequency of the vibration meaning that the frequency may be higher or lower after the controlling. In one example, the frequency remains the same after the controlling. In the example of FIG. 5A, the frequency is higher after the controlling. Higher frequency may help the user 100 to better detect the haptic output. However, in some cases a lower frequency is better as the higher frequency caused haptic output may be irritating to the user 100.

Referring to FIG. 5B, the ATA 300 may control the amplitude of the vibration. Increased amplitude of the vibration may cause a stronger haptic output. It may be beneficial to produce a stronger haptic output when the user 100 is, for example, exercising. On the other hand vibration with a smaller amplitude may be detectable when the user 100 is sitting or stationary.

Referring to FIG. 5C, the ATA 300 may control the sequence of the vibration. It may be beneficial to change the sequence based on activity of the user 100. For example, one or two vibrations may be enough when the user 100 is stationary, but during exercise it may be beneficial to output a vibration having three vibrations as shown in FIG. 5C.

Referring to FIG. 5D, the ATA 300 may control duration of the vibration. This may relate to the controlling the sequence as in FIG. 5C. However, in some cases it may be beneficial to, for example, repeat the same vibration sequence for two or more times. In another example, when the frequency changes, the duration of the vibration may become shorter or longer if same amount of vibrations is produced. Longer lasting vibration may be more easily detected by the user 100, but in some cases it may be irritating for the ATA 300 to vibrate too long when a shorter vibration is also detectable. Again when the user 100 is stationary a shorter vibration may suffice, but during a physical exercise longer vibration may be better.

Figure 5F:
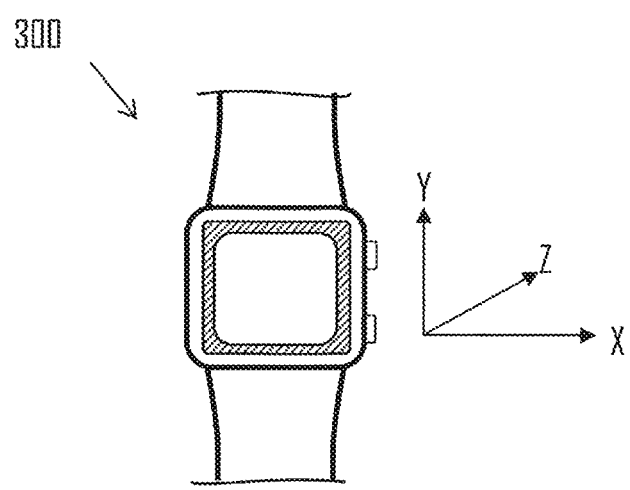

Referring to FIGS. 5E to 5F, the ATA 300 may control dimension of the vibration. For example, the vibration may first be substantially on X-axis and after the controlling the vibration may be substantially on Y-axis as shown in the example of FIG. 5E. In a way it may be understood that the direction of the vibration may be controlled. However, as the vibration may be back and forth motion, the direction may not be restricted to only one direction but to one dimension (i.e. to first direction and to a second direction being opposite to the first direction). Also, more than one dimensional vibration may be produced. That is, there may be two or three dimensional vibration produced by the haptic member 300.

It needs to be understood that the vibration produced by the haptic member may be one-dimensional, and/or multidimensional (e.g. two or three dimensional). Thus, the controlling may relate to changing the dimension, adding a dimension or removing a dimension of the vibration. Multidimensional vibration may be produced by the haptic member 330 comprising one or more vibration motors and/or one or more LRAs. For example, the vibration may be produced on X, Y, and Z-axes. This may be achieved, for example, by using three vibration motors such that each vibration motor produces the vibration on one of the axes. However, the implementation may vary.

Let us take as an example the wrist device 102. When it is worn by the user 100 on his/her wrist, the multidimensional vibration may mean that one vibration dimension is towards (i.e. perpendicular to the skin of the user 100) the skin of the user 100. This may be referred to as Z-axis. X-axis may be substantially parallel to fingers of the user 100. Y-axis may thus be perpendicular to Z and X-axes. It may be easy to understand that in such case dimension of the vibration may have an effect on how the user 100 perceives the haptic output. Thus, dimension of the vibration may be used to indicate different events of the ATA 300, for example. It may be possible to indicate, for example, a phone call with one dimension and a text message with another dimension. Naturally, other characteristics of the vibration may also vary between different events. Also, it may be possible to use different vibration dimension, for example, when the user is exercising compared to that when the user is stationary.

Figure 6A:
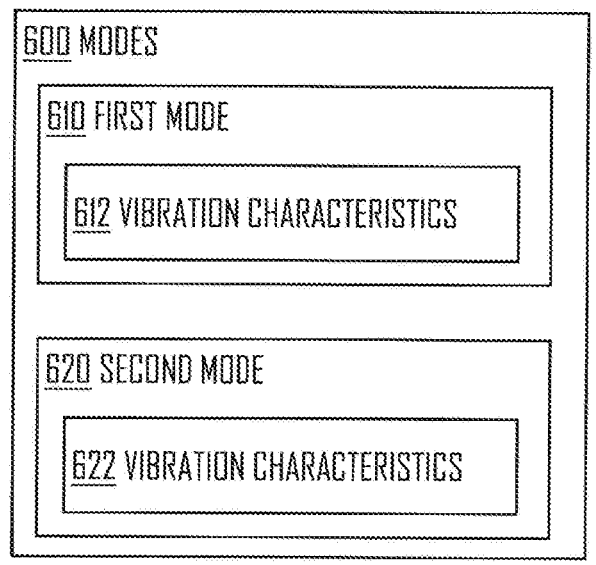
FIGS. 6A to 6C illustrate some embodiments.
Figure 6B:
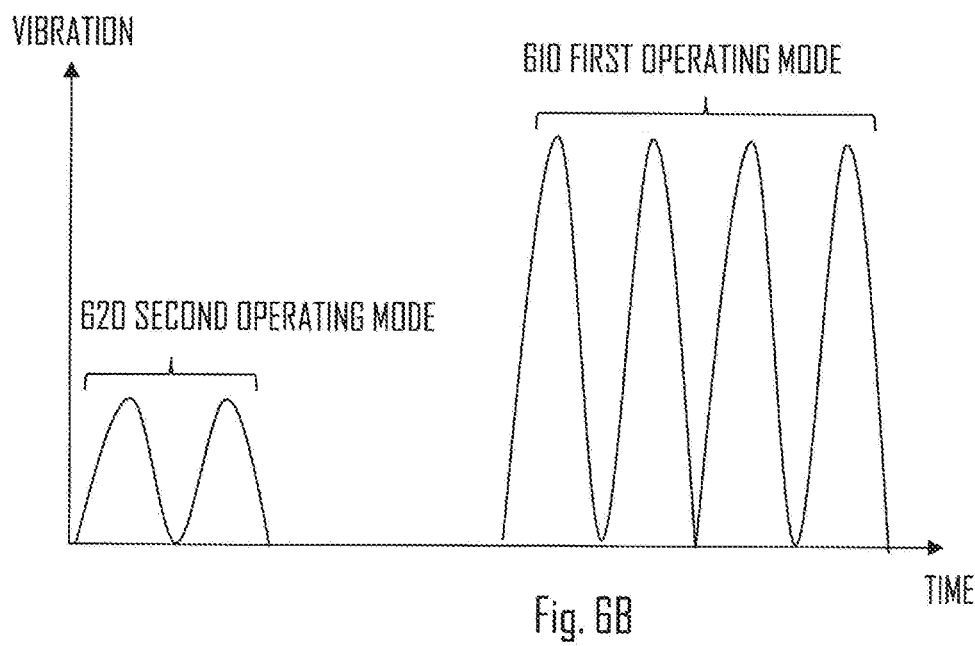
Figure 6C:
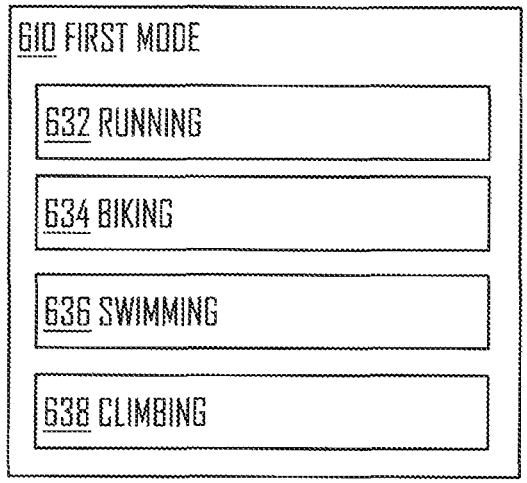

FIGS. 6A to 6C illustrate some embodiments. Referring to FIG. 6A, The ATA 300 may comprise a first and a second modes 610, 620, wherein the characteristics of the vibration 612, 622 is configurable in the first mode 610 and in the second mode 620 respectively. The characteristics of the vibration 612, 622 may comprise at least the characteristics described in relation to FIGS. 5A to 5F.

The ATA 300 may comprise a plurality of modes 600 (i.e. operation modes), wherein for each mode (e.g. modes 610, 620) the characteristics of the vibration may be configurable. For example, the second mode 620 may be used or active when the ATA 300 determines that the user 100 is performing everyday activities (e.g. working, watching TV, reading, attending a meeting). In such case, the vibration may need to be discreet (e.g. smaller amplitude, lower frequency, shorter duration, less vibration dimensions). However, when the ATA 300 determines that the user is performing physical exercise or similar activity, it may enter the first mode 610. In the first mode 610 the vibration may need to be more significant (e.g. larger amplitude, higher frequency, longer duration, more dimensions) compared with the second mode 620. Thus, for example, it may be possible that the ATA 300 determines based on the motion data that the user is performing everyday activities or being passive and enter the second mode 620. On the other hand the ATA 300 may determine that the user 100 is exercising or being otherwise active, based on the motion data, cardiac activity data and/or user input, and enter the first mode 610, wherein in the first mode 610 the vibration may be configured to be more remarkable compared with the second mode 620.

Referring to FIG. 6B, the controlling the characteristics of the vibration, by the ATA 300, comprises controlling the vibration such that the amplitude of the vibration is higher when the ATA 300 is in the first mode 610 compared with the ATA 300 being in the second mode 620. Similarly, duration of the vibration may be longer and/or frequency of the vibration may be higher in the first mode 610 compared with the second mode 620.

In an embodiment, the ATA 300 enters the first mode 610 in order to monitor training or physical exercise of the user 100 of the ATA 300. Training here may refer to performing sports, such as running, swimming or biking, to name a few.

Referring to FIG. 6C, the first mode 610 comprises a plurality of training modes 632-638, wherein the characteristics of the vibration is configurable in each of the plurality of training modes 632-638 respectively. Thus, the vibration and consequently the haptic output may be different during different sports. The ATA 300 may determine the training mode (e.g. the sports) based on the motion data, cardiac activity data and/or user input. For example, certain motion of the ATA 300 may reveal the current activity and/or sports.

In an embodiment, the plurality of training modes 632-638 are comprised in the ATA 300. Thus, there may not be a need for the first mode 610 and/or the second mode 620. The plurality of training modes 632-638 may comprise one or more training modes and one or more other modes. The other modes may comprise, for example, a mode that is used when the ATA 300 determines that the user 100 is not training. The other modes may comprise a sleep mode, a walking mode, and/or a meeting mode, to name a few examples. To sum it up, the ATA 300 may comprise one or more operating modes in which for each of said modes the haptic output may be configurable. On the other hand, there may be training specific modes as described above. It may be beneficial to have controllable haptic output for different sports as the intensity of the exercise may vary. Further, the haptic output may be controllable based on the intensity of the training. Thus, for example, for running mode there may be one or more subsets in which the haptic output may be controllable. For example, for high intensity training the haptic output may be beneficial to be different compared to low intensity running.

In an embodiment, the ATA 300 comprises a mode in which the vibration is not produced. Thus, no haptic output is outputted. For example, the ATA 300 may determine that the user is sleeping based on the motion data and/or cardiac activity data (e.g. heart rate, respiratory rate). Thus, the ATA 300 may control the vibration such that only very minimal vibration is produced, or that the vibration is not produced at all.

In an embodiment, the controlling the characteristics of vibration causing the haptic output comprises reducing the vibration substantially to zero. For example, the ATA 300 may prevent the vibration altogether such that for an event vibration is not produced. For example, during sleep the ATA 300 may determine that not vibration is needed.

In an embodiment, the controlling the characteristics of vibration causing the haptic output comprises increasing the vibration from a substantially zero value to a detectable value. For example, the ATA 300 may determine that the vibration is controlled to substantially zero value (e.g. user 100 is sleeping), and further determine that the user 100 needs to be alarmed (e.g. wake-up alarm), and control the vibration such that a detectable haptic output is produced.

In an embodiment, the controlling of the vibration is further based on the cardiac activity data. For example, during intense training it may be beneficial to output stronger haptic output. The intensity of the training may be determined from the motion data and/or from the cardiac activity data.

Figure 7A:
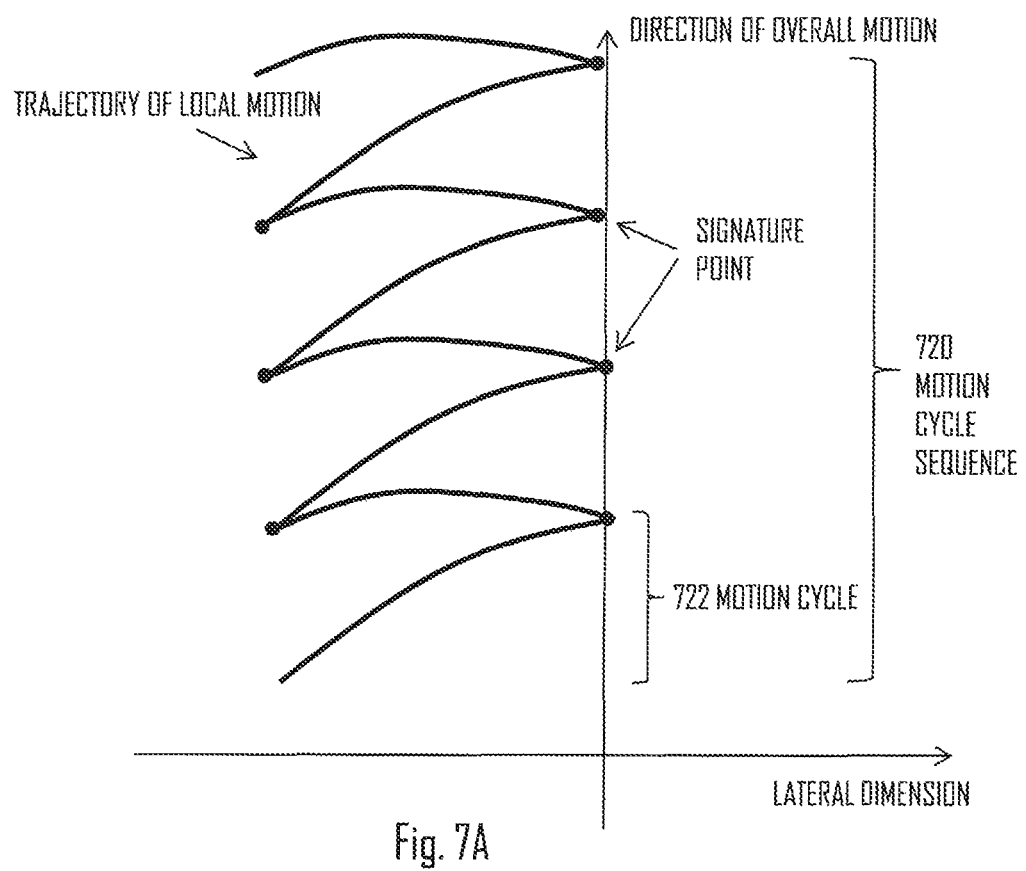
FIGS. 7A to 7C illustrate some embodiments.
Figure 7B:
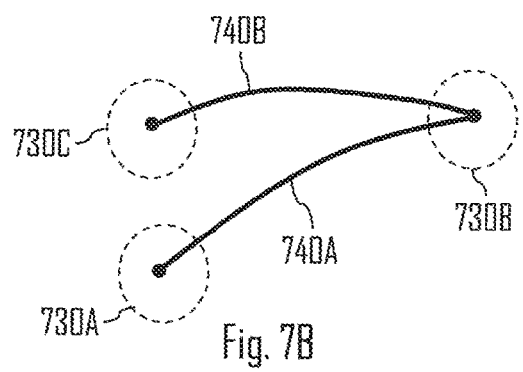
Figure 7C:
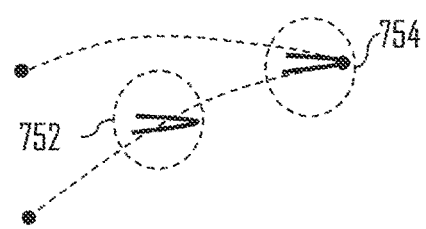

FIGS. 7A to 7C illustrate some embodiments. Referring to FIG. 7A, a motion cycle sequence 720 of the ATA 300 comprising one or more motion cycles 722 may be shown. The motion cycle 722 may, for example, be a motion cycle of a wrist device during an arm-swing sequence when the user 100 is walking or running. The motion cycle sequence 720 is illustrated with a trajectory of local motion. The direction of overall motion may be shown as the Y-axis. The trajectory of the local motion may be determined by using the motion circuitry 372, for example. For example, accelerometer and/or gyroscope may be used to determine the local motion. Also satellite positioning data may be used to determine the local motion. The direction of overall motion may be determined using, for example, satellite positioning data and/or magnetometer. Also it may be possible to determine the direction from the local motion. Using more than one method may improve the accuracy of the direction estimation.

The local motion may be characterized by signature points (shown in FIG. 7A) which may indicate the points wherein the direction of the local motion changes most significantly during the motion cycle 722. These signature points may be determined from the motion data, and thus the motion cycle 722, and consequently the motion cycle sequence, may be determined by the ATA 300.

Looking at FIG. 7B, one motion cycle (e.g. the motion cycle 722) is illustrated. The motion cycle may comprise a first part 740A, 740B, and a second part 730A, 730B, 730C, for example. The second part 730A, 730B, 730C may comprise more than one subpart, wherein the subparts are substantially at the signature points. The first part 740A, 740B may also comprise subparts which may be located between the signature points, as shown in FIG. 7B.

In an embodiment, the controlling the characteristics of the vibration causing the haptic output, by the ATA 300, comprises controlling the vibration such that the vibration is produced substantially during the first part 740A, 740B of the motion cycle of the ATA 300, wherein an absolute value of acceleration of the ATA 300 during the first part 740A, 740B is less than an absolute value of acceleration of the ATA 300 during a second part 730A, 730B, 730C of the motion cycle. Thus, it may be beneficial to produce the haptic output between the signature points which indicate the substantial change of direction of the ATA 300.

One example of haptic output during a motion cycle may be shown in FIG. 7C. For example, the vibration 752 causing the haptic output may be produced during the first part 740A, 740B as suggested in relation to FIG. 7B. On the other hand, the vibration 754 may be produced during the first part 730A, 730B, 730C. Producing the vibration 752 during the first part 740A, 740B may enable the user 100 to even better detect the haptic output as the direction of the movement of the ATA 300 during the first part 740A, 740B remains substantially the same or at least does not dramatically change. That is, the acceleration is not as high as during the second part 730A-C.

In an embodiment, the controlling the characteristics of the vibration causing the haptic output, by the ATA 300, comprises controlling the vibration such that the vibration is produced during a motion cycle of the ATA 300, wherein the vibration is substantially produced between the signature points of the motion cycle. Thus, in some embodiments, the vibration is not substantially produced during the signature points. However, in some embodiments, the vibration may be produced during the signature points.

It needs to be understood that the vibration causing the haptic output may comprise one or more vibrations produced in a sequence. Example of this may be shown in FIG. 5C, wherein there is first a sequence of two vibrations followed by the controlling step. After the controlling step there is shown a sequence of three vibrations. In an embodiment, the controlling the characteristics of the vibration causing the haptic output, by the ATA 300, comprises controlling the vibration such that the vibration is produced in a sequence, wherein the produced vibration sequence comprises one or more vibration subsets. Each subset may comprise, for example, one back and forth motion on at least one axis.

Figure 8A:
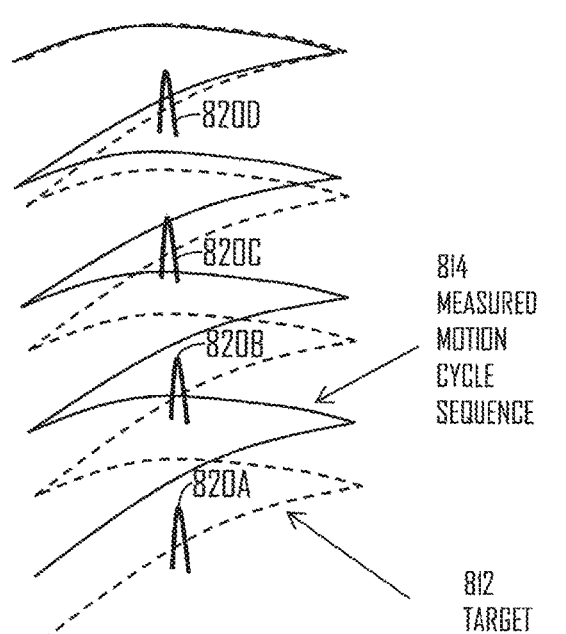
FIGS. 8A to 8B illustrate some embodiments.
Figure 8B:
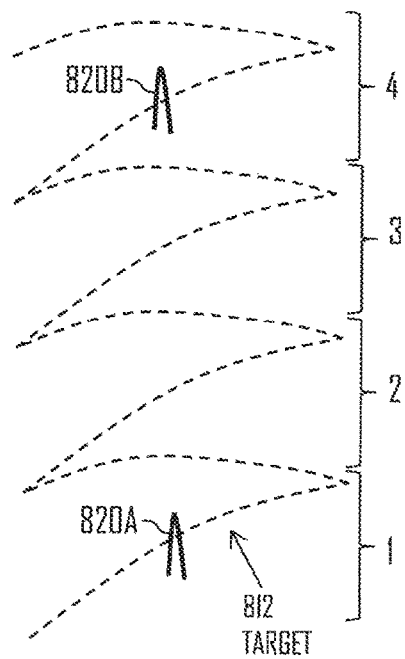

FIGS. 8A to 8B illustrate some embodiments. Referring to FIG. 8A a target motion cycle sequence 812 and a measured motion cycle sequence 814 may be shown. In an embodiment, the ATA 300 controls the vibration sequence such that the one or more vibration subsets 820A-D are produced according to the target motion cycle sequence 812. For example, a vibration subset 820A may be produced during one motion cycle of the target motion cycle sequence 812. Similarly, the other subsets 820B-D may be outputted during the motion cycles as shown in FIG. 8A.

In an embodiment, each vibration subset 820A-D corresponds to a motion cycle of the target motion cycle sequence 812. Thus, the ATA 300 may produce one vibration subset for one motion cycle, for example.

In an embodiment, each vibration subset 820A-D corresponds to every second, every fourth, or every eight motion cycle of the target motion cycle sequence 812. Example of producing the vibration subset 820A-B on every fourth motion cycle may be shown in FIG. 8B.

In an embodiment, the target motion cycle sequence represents a target running cadence, a target swimming cadence, and/or a target cycling cadence. For example, running cadence may mean the number of times user's foot strikes the ground in a given time period, usually measured per minute. Similarly, cadence may be determined for swimming (e.g. strokes per minute) or for cycling. In a way it may be understood that the haptic output according to the target cadence acts as a metronome for the user 100 to be in a right rhythm. As described above, the target cadence may be outputted such that one vibration subset is produced for every motion cycle or for every fourth motion cycle, for example. Looking at the example of FIG. 8A, the measured motion cycle 814 sequence may become closer to the target motion cycle sequence 812 as the user may become aware (by the haptic output) of the desired motion cycle sequence (e.g. cadence for running).

In an embodiment, the controlling the characteristics of the vibration causing the haptic output, by the ATA 300, comprises controlling the vibration such that more than one subset of the vibration sequence occurs within a current motion cycle and/or within a target motion cycle of the target motion cycle sequence. Example of this may be seen in FIG. 7C, where two vibration subsets 752, 754 may be outputted during one motion cycle sequence. This may enable the haptic output to be more easily detectable. It needs to be understood that during one motion cycle sequence there may be a number of vibration subsets, and thus the number may not be restricted to only one subset. Further, the subsets may be consecutive to each other or there may be a pause between different subsets.

In an embodiment, the ATA 300 determines frequency of a motion cycle sequence of the user 100. The frequency may be determined based on the motion data from the motion circuitry 372. The ATA 300 may then control the vibration such that the frequency of the vibration is different to that of the frequency of the motion cycle sequence. Thus, the ATA 300 may be configured to, based on the motion data, control the vibration frequency such that it differs from the measured motion cycle sequence.

In an embodiment, the ATA 300 is comprised in a portable bike computer. The bike or the computer may comprise haptic elements which may be caused to provide haptic output.

In an embodiment, the ATA 300 causes the vibration element to produce the vibration after the vibration has been controlled (e.g. frequency is changed). The ATA 300 may keep on obtaining the motion data, and further control, based on the motion data, the produced vibration. For example, the vibration may have an effect on the motion measurement of the ATA 300, and thus it may be beneficial to further adjust or control the vibration. Thus, the ATA 300 may keep controlling the vibration as the vibration is produced.

In an embodiment, the ATA 300 is the wrist device 102. It may be beneficial to use the vibration control in the wrist device 102 as the movement of a hand may cause a need to control the vibration. Further, using the motion circuitry in the wrist device 102 may enable the motion of the user 100 to be determined in an efficient manner. For example, it may be determined if the user 100 is running, walking or stationary, and thus vibration suitable for each situation may be produced. That is, during running the vibration may have a higher amplitude compared with the user being stationary. As described, the vibration may cause the haptic indication to the user 100. Higher amplitude may mean stronger haptic output. Thus, lower amplitude may mean a weaker haptic output. Haptic output may be beneficial to be induced to the wrist of the user 100.

According to yet another embodiment, the apparatus carrying out the embodiments comprises a circuitry including at least one processor and at least one memory including computer program code. When activated, the circuitry causes the apparatus to perform at least some of the functionalities according to any one of the embodiments, or operations thereof. For example, the method described in relation to FIG. 2 may be performed by the circuitry.

In an embodiment, an apparatus (e.g. ATA 300 or part of the ATA 300) carrying out the embodiments comprises means for performing the method according to any one of the embodiments, or operations thereof.

In an embodiment, there is provided a computer program product comprising program instructions which, when loaded into an apparatus, execute the method according to any one of the embodiments, or operations thereof. In an embodiment, there is provided a computer readable medium comprising said computer program.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

In an embodiment, at least some of the functionalities according to any one of the embodiments or operations thereof may be carried out by an apparatus comprising corresponding means for carrying out at least some of the described processes. Some example means for carrying out the processes may include at least one of the following: detector, processor (including dual-core and multiple-core processors), digital signal processor, controller, receiver, transmitter, encoder, decoder, memory, RAM, ROM, software, firmware, display, user interface, display circuitry, user interface circuitry, user interface software, display software, circuit, antenna, antenna circuitry, and circuitry. In an embodiment, the at least one processor, the memory, and the computer program code form processing means or comprises one or more computer program code portions for carrying out one or more operations according to any one of the embodiments or operations thereof.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, described with regard thereto, and they are not limited to the precise configurations set forth in the given figures, as will be appreciated by one skilled in the art.

Embodiments as described may also be carried out in the form of a computer process defined by a computer program. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The distribution medium may be non-transitory and/or transitory, for example. The computer program medium may be, for example but not limited to, a record medium, computer memory, read-only memory, electrical carrier signal, telecommunications signal, and software distribution package, for example. Coding of software for carrying out the embodiments as shown and described is well within the scope of a person of ordinary skill in the art.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

What is claimed is:

1. A method in an activity tracking apparatus configured to be worn by a user, the method comprising:
   obtaining, by the activity tracking apparatus, motion data from one or more sensors, the motion data characterizing motion of the activity tracking apparatus; and
   controlling, based on the motion data, characteristics of a vibration causing a haptic output, wherein the haptic output is configured to be output as a response to an event on the activity tracking apparatus,
   wherein the activity tracking apparatus comprises a plurality of modes, the characteristics of the vibration being configurable in each of the plurality of modes respectively,
   wherein the controlling of the characteristics of the vibration causing the haptic output comprises controlling, in a first mode of the plurality of modes, the vibration such that the vibration is produced substantially between signature points during a first part of a motion cycle of the activity tracking apparatus, the motion of the activity tracking apparatus changing direction most significantly during the motion cycle at the signature points, wherein an absolute value of acceleration of the activity tracking apparatus during the first part of the motion cycle is less than an absolute value of acceleration of the activity tracking apparatus during a second part of the motion cycle.

2. The method of claim 1, wherein the vibration is produced by a haptic member of the activity tracking apparatus.

3. The method of claim 2, wherein the vibration is produced by the haptic member such that the haptic output is transferred via a body, a display, and/or a fastening strap of the activity tracking apparatus.

4. The method of claim 2, wherein the vibration causes at least one element of the activity tracking apparatus to produce audible sound according to the vibration.

5. The method of claim 1, wherein the one or more sensors are comprised in the activity tracking apparatus, and wherein the one or more sensors comprise at least one of an acceleration sensor, gyroscope, magnetometer, satellite positioning circuitry, radio communication circuitry.

6. The method of claim 1, wherein the controlling the characteristics of the vibration causing the haptic output comprises controlling at least one of amplitude of the vibration, frequency of the vibration, sequence of the vibration, duration of the vibration, dimension of the vibration.

7. The method of claim 1, wherein the activity tracking apparatus comprises a first mode and a second mode, and wherein the characteristics of the vibration is configurable in the first mode and in the second mode respectively.

8. The method of claim 7, wherein the controlling the characteristics of the vibration comprises controlling the vibration such that the amplitude of the vibration is higher when the activity tracking apparatus is in the first mode compared with the activity tracking apparatus being in the second mode.

9. The method of claim 7, wherein the activity tracking apparatus enters the first mode in order to monitor physical training of a user of the activity tracking apparatus.

10. The method of claim 7, wherein the first mode comprises a plurality of physical training modes, and wherein the characteristics of the vibration is configurable in each of the plurality of physical training modes respectively.

11. The method of claim 1, wherein the controlling the characteristics of the vibration causing the haptic output comprises controlling, in a first mode of the plurality of modes, the vibration such that the vibration is produced in a sequence, and wherein the produced vibration sequence comprises one or more vibration subsets.

12. The method of claim 11, further comprising:
controlling the vibration sequence such that the one or more vibration subsets are produced according to a target motion cycle sequence.

13. The method of claim 12, wherein the target motion cycle sequence represents at least one of a target running cadence, a target swimming cadence, a target cycling cadence.

14. An apparatus comprising
at least one processor, and
at least one memory comprising a computer program code, wherein the at least one memory and the computer program code are configured, with the at least one processor, to cause an activity tracking apparatus to perform operations comprising:
obtaining motion data from one or more sensors, the motion data characterizing motion of the activity tracking apparatus; and
controlling, based on the motion data, characteristics of a vibration causing a haptic output, wherein the haptic output is configured to be output as a response to an event on the activity tracking apparatus,
wherein the activity tracking apparatus comprises a plurality of modes, the characteristics of the vibration being configurable in each of the plurality of modes respectively,
wherein the controlling of the characteristics of the vibration causing the haptic output comprises controlling, in a first mode of the plurality of modes, the vibration such that the vibration is produced substantially between signature points during a first part of a motion cycle of the activity tracking apparatus, the motion of the activity tracking apparatus changing direction most significantly during the motion cycle at the signature points, wherein an absolute value of acceleration of the activity tracking apparatus during the first part of the motion cycle is less than an absolute value of acceleration of the activity tracking apparatus during a second part of the motion cycle.

15. The apparatus of claim 14, wherein the apparatus is the activity tracking apparatus, the apparatus further comprising:
a haptic member configured to produce the vibration causing the haptic output.

16. The apparatus of claim 15, wherein the controlling the characteristics of the vibration causing the haptic output comprises controlling at least one of amplitude of the vibration, frequency of the vibration, sequence of the vibration, duration of the vibration, dimension of the vibration.

17. The apparatus of claim 16, wherein the controlling the characteristics of the vibration comprises controlling the vibration such that the amplitude of the vibration is higher when the activity tracking apparatus is in a first mode of the plurality of modes compared with the activity tracking apparatus being in a second mode of the plurality of modes.

18. The apparatus of claim 17, wherein the activity tracking apparatus enters the first mode in order to monitor physical training of a user of the activity tracking apparatus.

19. A non-transitory computer readable storage medium comprising program instructions which, when executed by an activity tracking apparatus cause the activity tracking apparatus to perform operations comprising:
obtaining motion data from one or more sensors, the motion data characterizing motion of the activity tracking apparatus; and
controlling, based on the motion data, characteristics of a vibration causing a haptic output, wherein the haptic output is configured to be output as a response to an event on the activity tracking apparatus,
wherein the activity tracking apparatus comprises a plurality of modes, the characteristics of the vibration being configurable in each of the plurality of modes respectively,
wherein the controlling of the characteristics of the vibration causing the haptic output comprises controlling, in a first mode of the plurality of modes, the vibration such that the vibration is produced substantially between signature points during a first part of a motion cycle of the activity tracking apparatus, the motion of the activity tracking apparatus changing direction most significantly during the motion cycle at the signature points, wherein an absolute value of acceleration of the activity tracking apparatus during the first part of the motion cycle is less than an absolute value of acceleration of the activity tracking apparatus during a second part of the motion cycle.

* * * * *